(12) United States Patent
Chung et al.

(10) Patent No.: US 10,030,050 B2
(45) Date of Patent: Jul. 24, 2018

(54) PEPTIDE HAVING OSTEOCLAST DIFFERENTIATION AND ACTIVATION INHIBITION, AND USE OF SAME

(71) Applicant: CAREGEN CO., LTD., Anyang-si (KR)

(72) Inventors: Yong Ji Chung, Yongin-si (KR); Eun Mi Kim, Yongin-si (KR); Eung Ji Lee, Anyang-si (KR); A Reum Han, Icheon-si (KR); Hyun Jung Kwon, Busan (KR)

( * ) Notice: Subject to any disclaimer, the term of this patent is extended or adjusted under 35 U.S.C. 154(b) by 0 days.

(21) Appl. No.: 15/500,178

(22) PCT Filed: Aug. 5, 2014

(86) PCT No.: PCT/KR2014/007202
§ 371 (c)(1),
(2) Date: Jan. 30, 2017

(87) PCT Pub. No.: WO2016/017844
PCT Pub. Date: Feb. 4, 2016

(65) Prior Publication Data
US 2017/0260233 A1 Sep. 14, 2017

(30) Foreign Application Priority Data
Jul. 31, 2014 (KR) .................. 10-2014-0098362

(51) Int. Cl.
| | | |
|---|---|---|
| C07K 7/00 | (2006.01) |
| C07K 7/06 | (2006.01) |
| A61K 38/00 | (2006.01) |
| A61K 38/04 | (2006.01) |
| A61K 38/08 | (2006.01) |

(52) U.S. Cl.
CPC ............ C07K 7/06 (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,516,891 A | 5/1996 | Siwruk et al. | |
| 2002/0156000 A1 | 10/2002 | May et al. | |
| 2003/0219864 A1* | 11/2003 | Desjarlais ............ | C07K 14/525 435/69.1 |
| 2005/0266498 A1 | 12/2005 | Okamoto et al. | |
| 2014/0165223 A1 | 6/2014 | Ntouni et al. | |

FOREIGN PATENT DOCUMENTS

| | | |
|---|---|---|
| EP | 2 383 283 A2 | 11/2011 |
| JP | 2001-352986 A | 12/2001 |
| JP | 2003-531636 A | 10/2003 |
| JP | 2010-222300 A | 10/2010 |
| KR | 10-2008-0093334 A | 10/2008 |
| KR | 10-2009-0036758 A | 4/2009 |
| KR | 2010-0035240 A | 4/2010 |
| KR | 2011-0107552 A | 10/2011 |
| KR | 10-2011-0130044 A | 12/2011 |
| WO | WO-00/53740 A1 | 9/2000 |
| WO | WO-2006/135069 A1 | 12/2006 |
| WO | WO-2008/127066 A1 | 10/2008 |
| WO | WO-2013/093039 A1 | 6/2013 |
| WO | WO-2014/093406 A1 | 6/2014 |

OTHER PUBLICATIONS

Tokuriki et al., 2009, Curr. Opin. Struc. Biol. 19:596-604).*
Bhattacharya et al. (2017, PLoS ONE 12(3): e0171355, https://doi.org/10.1371/journal.pone.0171355).*
Baum et al. (2016, Clinic. Rev. Allerg. Immunol. 51:1-15).*
International Search Report dated Apr. 20, 2015 for International Patent Application No. PCT/KR2014/007202, Chung et al., "Peptide having Osteoclast Differentiation and Activation Inhibition, and Use of Same," filed Aug. 5, 2014 (12 pages).
Jimi et al., "Selective inhibition of NF-kappa B blocks osteoclastogenesis and prevents inflammatory bone destruction in vivo," Nat Med. 10(6):617-24 (2004).
Votta et al., "Peptide aldehyde inhibitors of cathepsin K inhibit bone resorption both in vitro and in vivo," J Bone Miner Res. 12(9):1396-406 (1997).
Furuya et al., "Stimulation of bone formation in cortical bone of mice treated with a receptor activator of nuclear factor-kappaB ligand (RANKL)-binding peptide that possesses osteoclastogenesis inhibitory activity," J Biol Chem. 288(8):5562-71 (2013).
Office Action dated Nov. 15, 2017 for Japanese Patent Application No. 2017-505139, Chung et al., "Peptide having osteoclast differentiation and activation inhibition, and use of same," filed Jul. 31, 2014 (9 pages).
Olmez et al., "Protein-peptide interactions revolutionize drug development," INTECH Open Science, Open Minds. Chapter 3:49-72 (2012).
Ta et al., "Structure-based development of a receptor activator of nuclear factor-kappaB ligand (RANKL) inhibitor peptide and molecular basis for osteopetrosis," Proc Natl Acad Sci USA. 107(47):20281-6 (2010).

(Continued)

*Primary Examiner* — Elizabeth C. Kemmerer
(74) *Attorney, Agent, or Firm* — Clark & Elbing LLP; Susan M. Michaud

(57) ABSTRACT

A peptide which is formed from an amino acid sequence selected from the group comprising amino acid sequences of SEQ ID NO: 1 to SEQ ID NO: 3, according to the present invention, has osteoclast differentiation and activation inhibition and is highly effective for preventing or treating bone diseases related to the destruction of the bone. A peptide, according to the present invention, reduces expression of cathepsin K and TRAP related to osteoclast differentiation, inhibits nuclear translocation of NF-kB, and ultimately inhibits osteoclast differentiation. Provided is a composition, for preventing or treating bone diseases, comprising the peptide.

17 Claims, 15 Drawing Sheets

(56) References Cited

OTHER PUBLICATIONS

Extended European Search Report dated Feb. 2, 2018 for European Patent Application No. 14898754.8, Chung et al., "Peptide Having Osteoclast Differentiation and Activation Inhibition, and Use of Same," filed Aug. 5, 2014 (9 pages).

* cited by examiner

PEPTIDE HAVING OSTEOCLAST DIFFERENTIATION AND ACTIVATION INHIBITION, AND USE OF SAME

TECHNICAL FIELD

This application claims priority to and the benefit of Korean Patent Application No. 10-2014-0098362 filed in the Korean Intellectual Property Office on 31 Jul. 2014, the entire contents of which are incorporated herein by reference.

The present invention relates to a peptide having an osteoclast differentiation and activity inhibitory ability and a use thereof.

BACKGROUND ART

Bones support the soft tissue and weight of the human body, and surround internal organs to protect the same from external shocks. The bones are also one of the important parts of the human body that structurally support muscles or organs and store calcium or other essential minerals, such as, phosphorus and magnesium, in the body. Therefore, after the completion of growth, adult bones repeat the formation and resorption procedures of removing old bones and substituting for new bones very dynamically and continuously, until death without stopping, thereby maintaining the balance therebetween. This is called bone remodeling. The turnover of bones by removing old bones and substituting for new bones is essential for the restoration of the bone microdamage caused by growth and stress and the appropriate maintenance of bone functions.

It has been known that two types of cells are greatly involved in bone remodeling: osteoblasts, which form bones; and osteoclasts, which destroy bones. The osteoblasts form a receptor activator of nuclear factor-κB ligand (RANKL) and a decoy receptor thereof, that is, osteoprotegerin (OPG). When RANKL binds to RANK, which is a receptor on a surface of osteoclast progenitor cells, the osteoclast progenitor cells mature into osteoclasts, resulting in bone resorption. However, the binding between OPG and RANKL blocks a binding between RANKL and RANK, thereby inhibiting the formation of osteoclasts and preventing unnecessary bone resorption. The resorption or destruction of old bones occurs by osteoclasts formed from blood cells (hematopoietic stem cells), and makes pores in the bones to release a small amount of calcium into the blood stream, and the calcium is used to maintain physical functions. Meanwhile, the osteoblasts formed from bone cells fill the pores with collagen and cover the precipitates (hydroxyapatite) of calcium and phosphor hydroxyapatite, thereby forming new solid bones and rebuilding the skeleton. It takes about 100 days until the bone is destroyed to form again into new bones. While 100% of the calcium content in bone is changed within 1 year in an infant, about 10-30% of the skeleton is rebuilt by the bone remodeling in an adult every year. Only if the osteoclastic rate is equal to the osteogenic rate, the bone density can be maintained as before. The imbalance in such important bones may cause many diseases, and particularly, the diseases associated with bone damage due to osteoporosis and bone metastasis of cancer cells are representative.

Osteoporosis is a disorder in which the bone mass is decreased by various causes and the risk of bone fracture is continuously increased due to the degeneration of microstructure in bone tissue. Also, osteoporosis is a condition in which the contents of minerals (e.g., calcium) and substrates of bone have been reduced, and osteoporosis occurs when the osteoclasis becomes superior to the osteogenesis to the imbalance of bone remodeling. The interiors of normal bones have dense structures like a mesh, but in the case of osteoporosis, the interval between the structures becomes wider, the microstructure becomes thinner and weakened, and thus, the bone progresses to a state where it can easily fracture by even a small impact. Osteoporosis causes rapid bone loss (2-3% each year) at the time of the beginning of menopause. Osteoporosis diseases are classified into: postmenopausal osteoporosis where the risk of spine compression and wrist bone fracture is increased; senile osteoporosis where it is developed slowly (0.5-1% a year) in elder men and women aged more than 70 years and induces gradual bone loss of hip and spine bones; and secondary osteoporosis wherein it is developed by diseases (endocrine diseases, gastrointestinal diseases, and malignant tumors), drugs (adrenal cortical hormones, anticancer chemotherapy, thyroid hormones, anticonvulsants, antiplatelets, methotexate, cyclosporine and GnRH), alcohol, smoking or accident, regardless of age.

Bisphosphonate-based therapeutics, such as Fosamax, (generic name: alendronate) and Actonel (generic name: risedronate), are being used for the bone damage caused by the above osteoporosis diseases and the bone metastasis of cancer cells. Most of these bisphosphonate-based preparations weaken the functions of osteoclasts destroying bones and induce the apoptosis thereof, thereby delaying or stopping the loss of bones. However, in patients taking bisphosphonates, these drugs do not have an action of promoting the formation of new bones, and the incidence of chronic necrosis (osteonecrosis), severe atrial fibrillation, neutralization of bones and joints, or musculoskeletal pain has been recently increasing year by year. Therefore, a lot of interest is concentrated on the development of preventive and therapeutic agents for osteoporosis, which promotes the bone formation rather than suppressing the bone resorption.

Throughout the entire specification, many papers and patent documents are referenced and their citations are represented. The disclosure of the cited papers and patent documents are entirely incorporated by reference into the present specification, and the level of the technical field within which the present invention falls and the details of the present invention are explained more clearly.

DETAILED DESCRIPTION OF THE INVENTION

Technical Problem

The present inventors endeavored to develop peptides having biologically effective activity, and as a result, the present inventors established that a peptide including an amino acid sequence of SEQ ID NO: 1, SEQ ID NO: 2, or SEQ ID NO: 3 has excellent effects of preventing and treating various bone diseases caused by bone destruction by inhibiting osteoclast differentiation and activity, and thus completed the present invention.

Therefore, an aspect of the present invention is to provide a peptide having an osteoclast differentiation and activity inhibitory ability.

Another aspect of the present invention is to provide a composition for preventing or treating bone diseases.

Other purposes and advantages of the present invention will become more obvious with the following detailed description of the invention, claims, and drawings.

Technical Solution

In accordance with an aspect of the present invention, there is provided a peptide having an osteoclast differentiation and activity inhibitory ability, the peptide including an amino acid sequence selected from the group consisting of amino acid sequences of SEQ ID NO: 1 to SEQ ID NO: 3.

The present inventors endeavored to develop peptides having biologically effective activity, and as a result, the present inventors established that a peptide including an amino acid sequence of SEQ ID NO: 1, SEQ ID NO: 2, or SEQ ID NO: 3 has excellent effects of preventing and treating various bone diseases caused by bone destruction by inhibiting osteoclast differentiation and activity.

The peptide of the present invention includes an amino acid sequence of SEQ ID NO: 1, SEQ ID NO: 2, or SEQ ID NO: 3. Specifically, the peptide of the present invention consists essentially of an amino acid sequence selected from the group consisting of amino acid sequences of SEQ ID NO: 1 to SEQ ID NO: 3.

The peptide of the present invention effectively inhibits the differentiation and activity of osteoclasts.

The bone destruction in joints occurs by the activation of osteoclasts, and myeloid precursor cells differentiating from hematopoietic stem cells is differentiated into the osteoclasts in an inflammatory environment. Many inflammatory cytokines and chemokines exist in rheumatoid joints, and these substances increase the expression of several molecules necessary for osteoclast differentiation, thereby inducing the formation of osteoclasts. It has been recognized that the main therapeutic purpose of rheumatoid arthritis is to suppress the bone destruction to minimize the joint damage.

The substances essential for the differentiation of myeloid progenitor cells into osteoclasts are the receptor activator of nuclear factor kappa κB (RANK), which is induced on the surface of the progenitor cells, and the receptor activator of nuclear factor κB ligand (RANKL), which is the ligand for RANK, and the binding of RANK and RANKL, the so-called RANK-RANKL interaction, is indispensable for osteoclast differentiation. In addition, the macrophage colony stimulating factor (M-CSF) also plays an important role in the mature and differentiation of osteoclasts. The RANK-RANKL interaction and M-CSF are indispensable for the main signaling pathway of osteoclast differentiation, but the ligands are bound to intracellular signal transducers DAP12 and FcRγ through several kinds of immunoglobulin-like receptors on the surface of the progenitor cells, thereby providing co-stimulatory signals. The most central signaling pathway is configured such that, after the RANKL-RANK interaction, NF-κB activation is induced through TNF-receptor-associated factor 6 (TRAF6), which is an intracellular signal transducer, thereby increasing the transcription of genes necessary for osteoclast formation. Next, M-CSF is also known to be a material that is essential for the osteoclast differentiation, and binds to a specific receptor, such as cFMS, which pertains to a receptor tyrosine kinase super family, to form a Src-PYK2 complex, which then induces a transcription regulatory material, such as NF-κB, or performs intracellular signaling through integrin proteins.

According to an embodiment of the present invention, the peptide of the present invention reduces the expressions of tartrate resistant alkaline phosphatase (TRAP) and cathepsin K in association with osteoclast differentiation and inhibits the nuclear translocation of NF-κB, ultimately inhibiting the differentiation and activity of osteoclasts.

As used herein, the term "peptide" refers to a linear molecule in which amino acid residues bind to each other via a peptide linkage. The peptide of the present invention may be prepared by chemical synthesis methods known in the art, especially, solid-phase synthesis techniques (Merrifield, J. Amer. Chem. Soc. 85:2149-54(1963); Stewart, et al., Solid Phase Peptide Synthesis, 2nd. ed., Pierce Chem. Co.: Rockford, 111(1984)) or liquid-phase synthesis techniques (U.S. Pat. No. 5,516,891).

According to an embodiment of the present invention, a protecting group, which is selected from the group consisting of an acetyl group, a fluorenyl methoxy carbonyl group, a formyl group, a palmitoyl group, a myristyl group, a stearyl group, and polyethylene glycol (PEG), may be linked to the N- or C-terminus of the peptide.

The foregoing amino acid modification significantly improves the stability of the peptide of the present invention. As used herein, the term "stability" refers to storage stability (e.g., room-temperature storage stability) as well as "in vivo" stability. The foregoing protecting group protects the peptides of the present invention from the attack of in vivo protein cleavage enzymes.

According to another aspect of the present invention, there is provided a composition for preventing or treating a bone disease, the composition containing, as an active ingredient, the foregoing peptide including an amino acid sequence selected from the group consisting of an amino acid sequence of SEQ ID NO: 1 to SEQ ID NO: 3.

Since the composition of the present invention contains, as an active ingredient, the foregoing peptide composed of an amino acid sequence of SEQ ID NO: 1, SEQ ID NO: 2, or SEQ ID NO: 3, of the present invention, the descriptions of overlapping contents therebetween will be omitted to avoid excessive complexity of the present specification.

As validated in the following examples, the peptide including an amino acid sequence of SEQ ID NO: 1, SEQ ID NO: 2, or SEQ ID NO: 3 of the present invention inhibits the differentiation and activity of osteoclasts, and thus is very effective in the prevention or treatment of a bone disease in association with bone destruction.

The composition for preventing or treating a bone disease of the present invention can be used for all diseases that occur from excessive osteoclastic action, and may be used for, for example, bone damage, osteoporosis, osteomalacia, rickets, fibrous osteitis, an aplastic bone disease, or a metabolic bone disease.

According to one embodiment of the present invention, the composition of the present invention may be prepared into a pharmaceutical composition containing: (a) a pharmaceutically effective amount of the foregoing peptide of the present invention; and (b) a pharmaceutically acceptable carrier.

As used herein, the term "pharmaceutically effective amount" refers to an amount sufficient to attain efficacy or activity of the foregoing peptide.

The pharmaceutically acceptable carrier contained in the pharmaceutical composition of the present invention is ordinarily used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil. The pharmaceutical composition of the present invention may further contain, in addition to the above ingredients, a lubricant, a wetting agent, a sweetening agent, a flavoring agent, an emulsifier, a suspending agent, a preservative, and the like. Suitable pharmaceutically acceptable carriers and agents are described in detail in *Remington's Pharmaceutical Sciences* (19th ed., 1995).

The pharmaceutical composition of the present invention may be administered orally or parenterally, and examples of the parenteral administration may include intravenous, subcutaneous, intramuscular, intraperitoneal, local, and transdermal injections.

A suitable dose of the pharmaceutical composition of the present invention may vary depending on various factors, such as the method for formulation, the manner of administration, the age, body weight, gender, and morbidity of the patient, the diet, the time of administration, the route of administration, the excretion rate, and response sensitivity. Meanwhile, the dose of the pharmaceutical composition of the present invention is 0.0001-200 µg per day.

The pharmaceutical composition of the present invention may be formulated into a unit dosage form or a multidose container using a pharmaceutically acceptable carrier and/or excipient according to the method easily conducted by a person having ordinary skills in the art to which the present invention pertains. Here, the dosage form may be a solution in an oily or aqueous medium, a suspension, an emulsion, an extract, a powder, granules, a tablet, a capsule, or a gel (e.g., a hydrogel), and may further include a dispersant or a stabilizer.

Advantageous Effects

Features and advantages of the present invention are summarized as follows:

(i) The peptide including an amino acid sequence selected from the group consisting of amino acid sequences of SEQ ID NO: 1 to SEQ ID NO: 3 has an osteoclast differentiation and activity inhibitory ability, and is very effective in the prevention or treatment of bone disease in association with bone destruction, (ii) The peptide of the present invention reduces the expressions of TRAP and cathepsin K in association with osteoclast differentiation and inhibits the nuclear translocation of NF-κB, ultimately inhibiting the differentiation and activity of osteoclasts.

(iii) The present invention provides a composition, containing the foregoing peptide, for preventing or treating a bone disease.

BRIEF DESCRIPTION OF THE DRAWINGS

FIG. 1A. Peptide of SEQ ID NO: 1, FIG. 1B. Peptide of SEQ ID NO: 2, FIG. 1O. Peptide of SEQ ID NO: 3

FIG. 2A. Peptide of SEQ ID NO: 1, FIG. 2B. Peptide of SEQ ID NO: 2, FIG. 2C. Peptide of SEQ ID NO: 3

FIG. 3A. Peptide of SEQ ID NO: 1, FIG. 3B. Peptide of SEQ ID NO: 2, FIG. 3C. Peptide of SEQ ID NO: 3

FIG. 4A. Peptide of SEQ ID NO: 1, FIG. 4B. Peptide of SEQ ID NO: 2, FIG. 4C. Peptide of SEQ ID NO: 3

FIG. 5A. Peptide of SEQ ID NO: 1, FIG. 5B. Peptide of SEQ ID NO: 2, FIG. 5C. Peptide of SEQ ID NO: 3

MODE FOR CARRYING OUT THE INVENTION

Figure 1A:
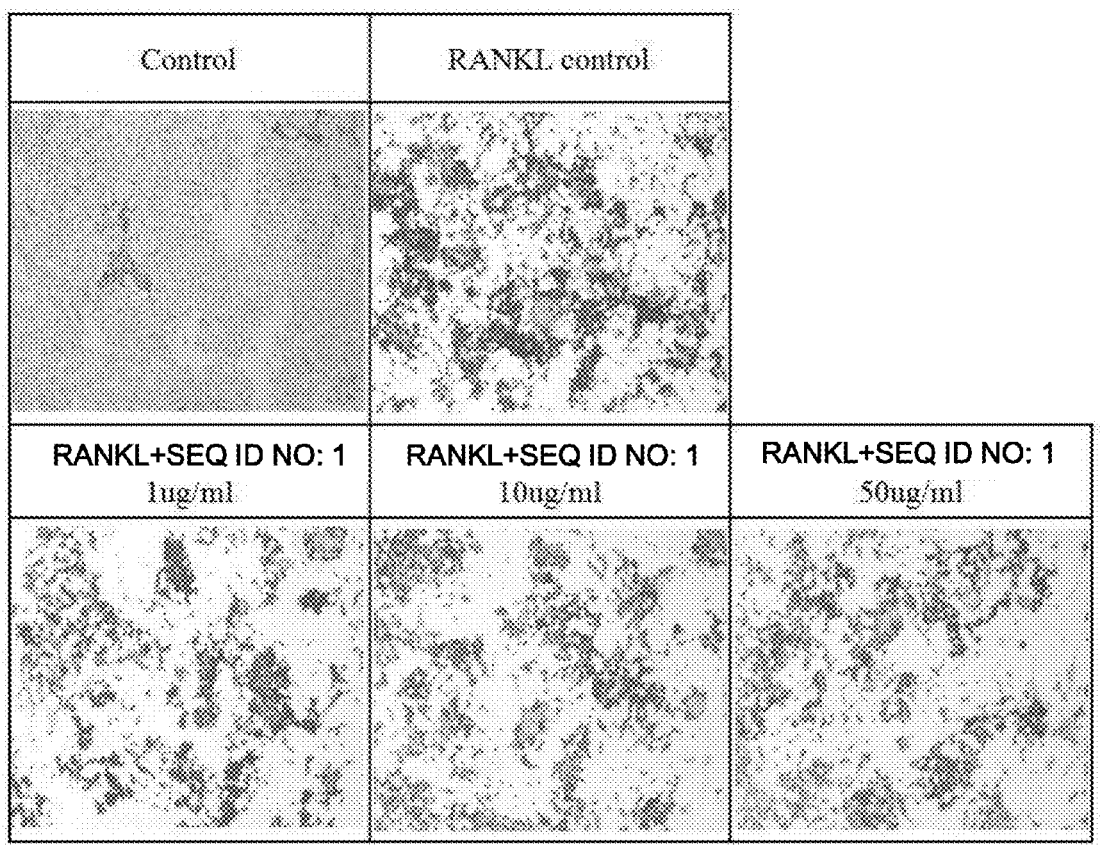
FIG. 1A-1C illustrates TRAP staining results verifying the changes in expression levels of TRAP protein during osteoclast differentiation, by the treatment with peptides of the present invention.

Hereinafter, the present invention will be described in detail with reference to examples. These examples are only for illustrating the present invention more specifically, and it will be apparent to those skilled in the art that the scope of the present invention is not limited by these examples.

EXAMPLES

Synthesis Example 1: Peptide Synthesis 700 mg of chloro trityl chloride resin (CTL resin, Nova Biochem Cat No. 01-64-0021) was put into a reaction container, and 10 ml of methylene chloride (MC) was added, followed by stirring for 3 minutes. After the solution was removed, 10 ml of dimethylform amide (DMF) was added, followed by stirring for 3 minutes, and then the solvent was again removed. 10 ml of a dichloromethane (DCM) solution was added into the reactor, and 200 mmole Fmoc-Arg(Pbf)-OH (Bachem, Swiss) and 400 mmole diisopropyl ethylamine (DIEA) were added, after which the mixture was well dissolved with stirring, followed by reaction with stirring for 1 hour. After the reaction, washing was conducted. Then, methanol and DIEA (2:1) were dissolved in DCM, followed by reaction for 10 minutes, and then washing was conducted with excessive DCM/DMF (1:1). After the solution was removed, 10 ml of DMF was added, followed by stirring for 3 minutes, and then the solvent was again removed. 10 ml of a deprotection solution (20% piperidine/DMF) was put into the reaction container, followed by stirring at room temperature for 10 minutes, and then the solution was removed. An equal amount of a deprotection solution was added, and then, again, the reaction was maintained for 10 minutes, followed by removal of the solution. Then, washing was conducted twice with DMF, once with MC, and once with DMF, for 3 minutes each, thereby preparing Arg(Pbf)-CTL Resin.

10 ml of a DMF solution was put in a new reactor, and 200 mmol Fmoc-Leu-OH (Bachem, Swiss), 200 mmol HoBt, and 200 mmole Bop were added, and the mixture was well dissolved with stirring. Then, 400 mmole N,N-diisopropylethylamine (DIEA) was divisionally put twice into the reactor, and then the stirring was conducted for at least 5 minutes until all solids were dissolved. The dissolved amino acid mixed solution was put in the reaction container containing the deprotected resin, and the reaction was conducted with stirring at room temperature for 1 hour. After the reaction liquid was removed, the stirring was conducted using a DMF solution three times for 5 minutes each, followed by removal. A small amount of the reacted resin was taken to check the reaction degree by the Kaiser test (Ninhydrin test). A deprotection reaction was conducted using the deprotection solution, twice, in the same manner as described above, thereby preparing Leu-Arg(Pbf)-CTL Resin. After sufficient washing with DMF and MC, the Kaiser test was again conducted, and then the following amino acid attachment test was conducted in the same manner as described above.

Based on the selected amino acid sequence, a chain reaction was conducted in the order of Fmoc-Phe, Fmoc-Glu(OtBu), Fmoc-Val, Fmoc-Pro, Fmoc-Ser(tBu). The Fmoc-protecting group was removed by reaction twice with a deprotection solution for 10 minutes for each, followed by well washing. Acetic anhydride, DIEA, and hydroxy benzotriazole (HoBt) were added to perform acetylation for 1 hour, and then the prepared peptidyl resin was washed three times sequentially with DMF, MC, and methanol, dried under the slow flow of nitrogen gas, and completely dried by vacuum-drying under phosphorus pentoxide ($P_2O_5$). Then, 30 ml of a leaving solution (95% trifluoroacetic acid (TFA), 2.5% distilled water, and 2.5% thioanisole) was added, and the reaction was maintained for 2 hours while the mixture was intermittently shaken at room temperature. The resin was obtained through filtration, washed with a small amount of a solution, and then mixed with stock solution. The resulting mixture was distilled using reduced pressure such that the total volume is reduced to about half, and then 50 ml of cold ether was added to induce precipitation. Thereafter, the precipitates were collected by centrifugation, followed by washing twice with cold ether. The stock solution was removed, followed by sufficient drying under nitrogen atmosphere, thereby synthesizing 0.80 g of unpurified peptide 1, Ser-Pro-Val-Glu-Phe-Leu-Arg (SEQ ID NO: 1, yield: 88.8%). From the measurement using a molecular weight analysis system, the molecular weight thereof was determined as 846.7 (theoretical value: 846.9). Through the above method, peptide 2, Ile-Thr-Leu-Gln-Glu-Ile-Ile-Arg-Thr (SEQ ID NO: 2) and peptide 3, Ala-Cys-Ile-His-Thr-Leu-Ser-Leu-Leu-Cys (SEQ ID NO: 3) were synthesized (yields: 86.4% and 83.2%, respectively). From the measurement using a molecular weight analysis system, the molecular weights thereof were determined as 1086.3 (theoretical value: 1086.3) and 1073.0 (theoretical value: 1073.3), respectively.

TABLE 1

| SEQ ID NO | Amio acid sequence | Analysis value (Mass Spectrometer) | |
|---|---|---|---|
| | | Anlaltical value | Thereoreticl value |
| 1 | Ser-Pro-Val-Glu-Phe-Leu-Arg | 846.7 | 846.9 |
| 2 | Ile-Thr-Leu-Gln-Glu-Ile-Ile-Arg-Thr | 1086.3 | 1086.3 |
| 3 | Ala-Cys-Ile-His-Thr-Leu-Ser-Leu-Leu-Cys | 1073.0 | 1073.3 |

Example 1: TRAP Staining

An attempt was made to verify the level of TRAP protein expressed during osteoclast differentiation through staining and observe the reduction tendency thereof during the treatment with peptides.

Raw 264.7 macrophages were seeded in a 48-well plate at $1 \times 10^4$ cells/well, and at the same time, treated with peptides with different concentrations (peptide alone or together with 50 ng/ml RANKL), and incubated for 5 days to induce differentiation. TRAP staining was conducted using the acid phosphatase kit (Sigma Aldrich). The fixation buffer was added, followed by reaction for 30 seconds and washing with distilled water. A staining solution was added at 200 ul per well, followed by reaction at 37° C. for 30 minutes and washing with distilled water. The resulting product was dried for one day, and then observed using a microscope.

Figure 1B:
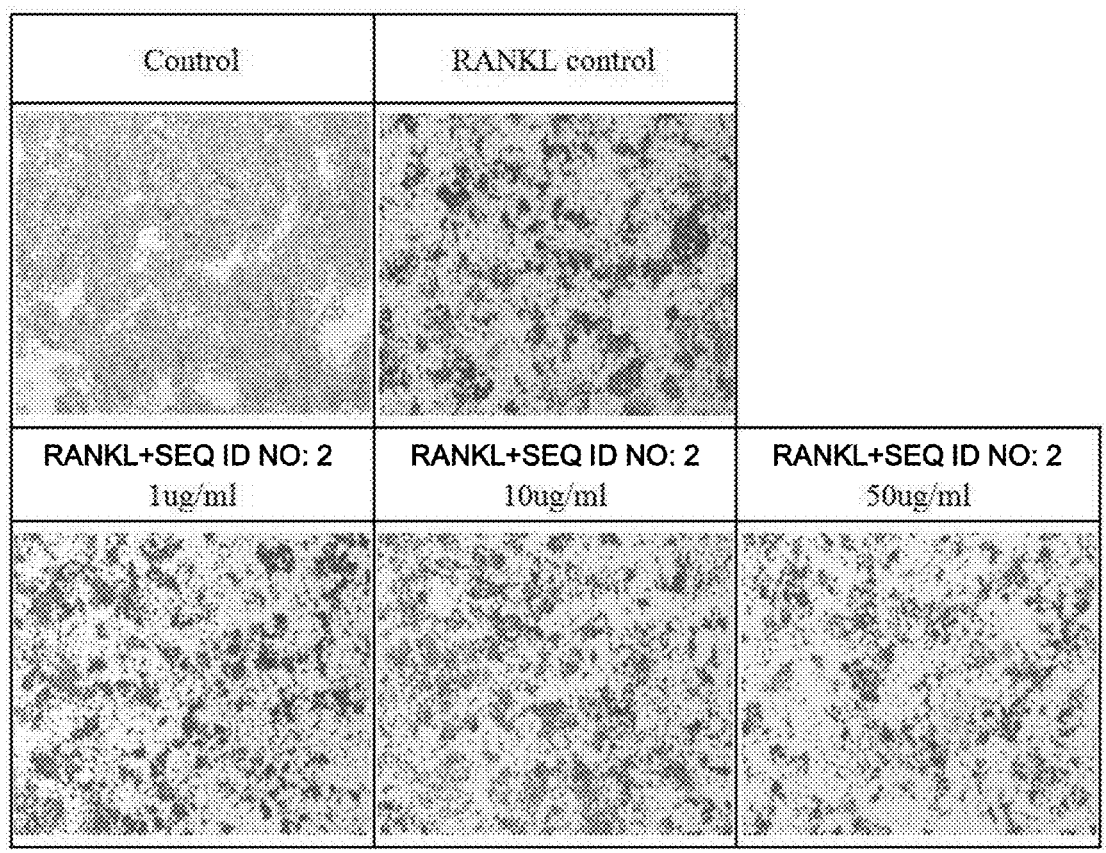
Figure 1C:
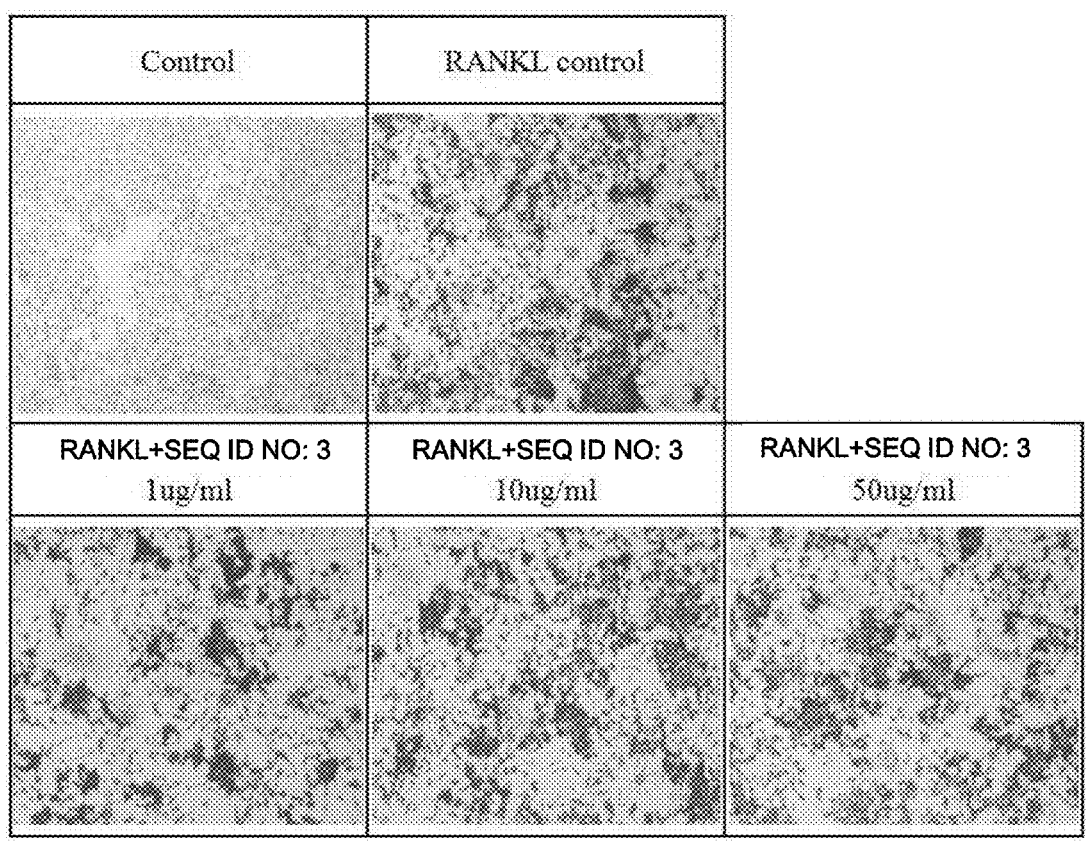

It was observed that, when compared with a control group in which osteoclast differentiation was induced by RANKL treatment to increase TRAP expression, the TRAP expression was reduced in a concentration-dependent manner in groups treated with peptides of SEQ ID NO: 1 to SEQ ID NO: 3 (FIGS. 1a to 1c).

Example 2: RT-PCR of TRAP and Cathepsin K

An attempt was made to verify the mRNA levels of TRAP and Cathepsin K expressed during osteoclast differentiation through RT-PCR and to observe the reduction tendencies thereof during the treatment with peptides were observed.

Figure 2A:
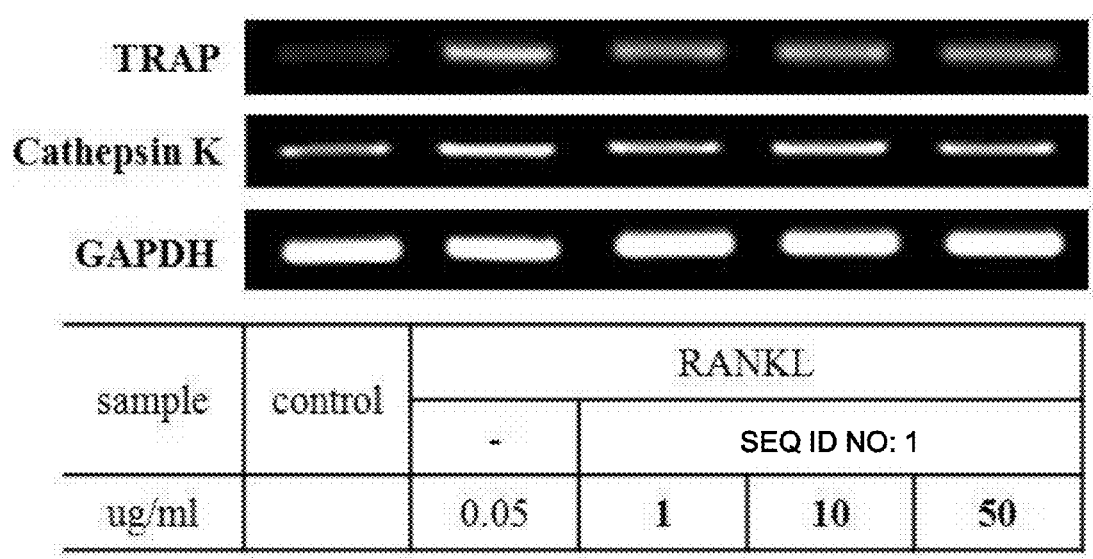
FIG. 2A-2C illustrates RT-PCR results verifying the mRNA levels of TARP and Cathepsin K expressed during osteoclast differentiation, by the treatment with peptides of the present invention.
Figure 2B:
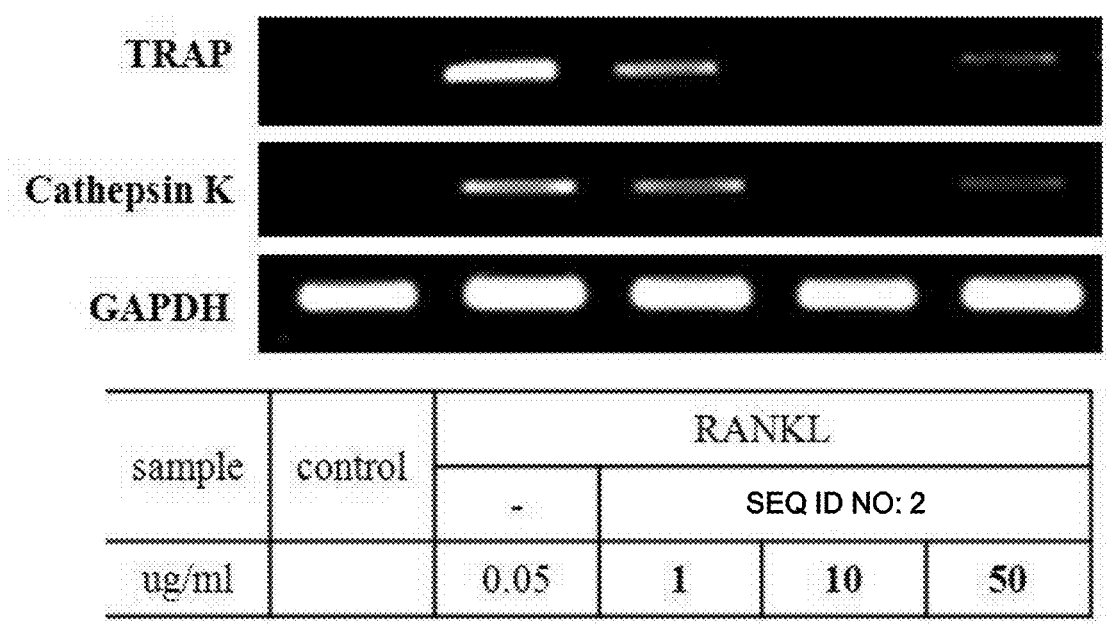
Figure 2C:
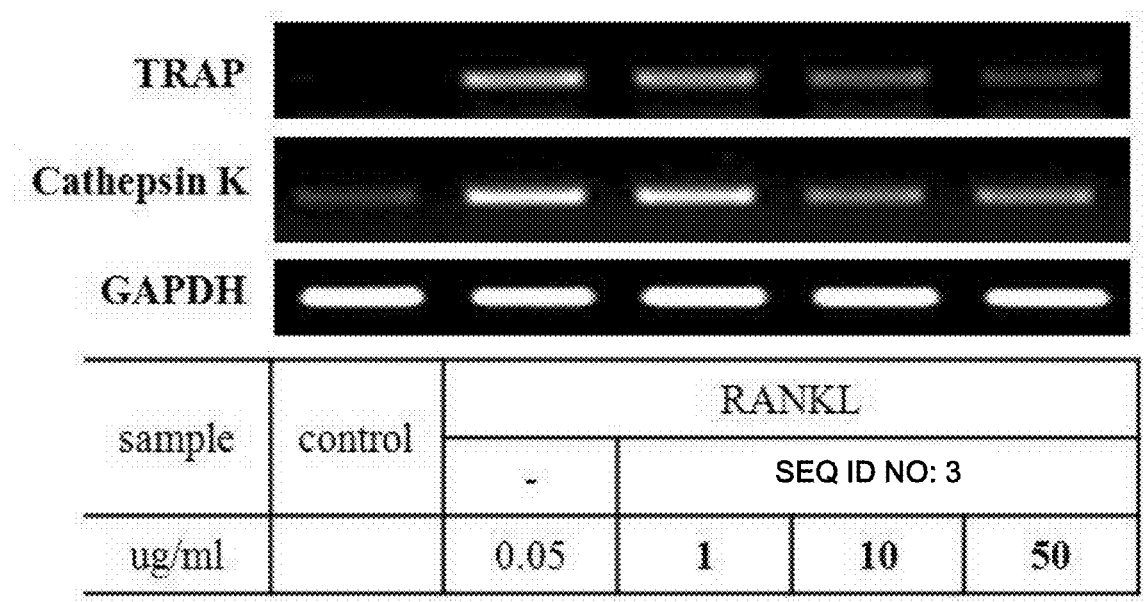

Raw 264.7 cells were seeded in a 48-well plate at a cell density of $1 \times 10^4$ cells/well. The cells were treated with 50 ng/ml RANKL and peptides with different concentrations (10 and 50 ug/ml), and incubated for 5 days in an incubator. After the incubation-completed cells were collected, the cells were treated with RNA extraction solution (Easy Blue, Intron) to prepare RNA, and then cDNA was synthesized using RT premix (Intron). PCR was carried out using primers with respect to respective markers (Cathepsin K and TRAP) and PCR premix (Intron). Then, 5 µl of PCR products were loaded on 1% agarose gel, followed by electrophoresis, and then the bands were investigated using Gel-Doc. It was observed that the expressions of TRAP and Cathepsin K, as osteoclast differentiation markers induced by RANKL treatment, were reduced by treatment with the peptides of SEQ ID NO:1 to SEQ ID NO: 3 (FIGS. 2a to 2c).

Example 3: Western Blot Analysis of NF-κB Translocation

In order to investigate the nuclear translocation of NF-κB promoted during osteoclast differentiation, an attempt was made to observe the increase of NF-κB level in the nucleus by RANKL treatment after the isolation of nuclear proteins and observe the reduction tendency thereof by the treatment with peptides.

Mouse macrophage line Raw 264.7 macrophages were seeded in a 6-well plate at a cell density of $5 \times 10^5$ cells/well. The cells were incubated over one night, and then a medium was exchanged with a serum-free medium, followed by incubation for 6 hours. The cells were treated with 50 ng/ml RANKL and materials, followed by incubation for 30 minutes. Nuclear proteins were extracted from the treatment-completed cells, followed by BCA quantification, and then samples were prepared and subjected to electrophoresis on SDS-PAGE. The nuclear proteins were transferred onto a nitrocellulose membrane, and then blocked using 5% skim milk for 1 hour. Primary antibody, anti-NF-κB p65 was diluted in a blocking solution at 1:1,000, and incubated overnight in a refrigerator. After washing three times with PBST for 15 minutes for each, the cells were incubated using secondary antibody anti-rabbit IgG-HRP at room temperature for 1 hour. The cells were washed with PBST for 15 minutes three times for each, and then the color development was conducted using ECL solution.

Figure 3A:
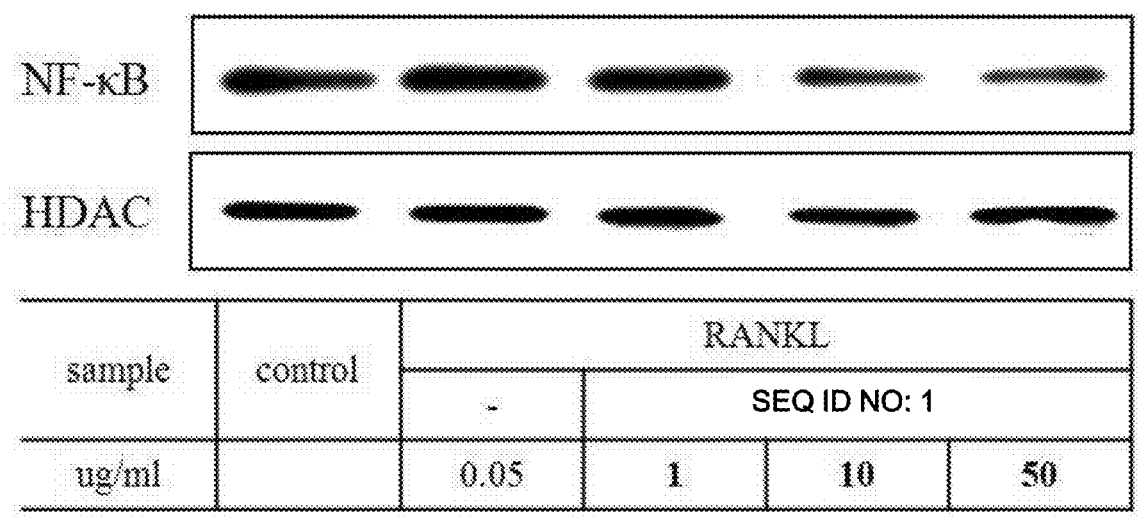
FIG. 3A-3C illustrates western blotting results verifying the changes in nuclear translocation of NF-κB, promoted during osteoclast differentiation, by the treatment of the peptides of the present invention.
Figure 3B:
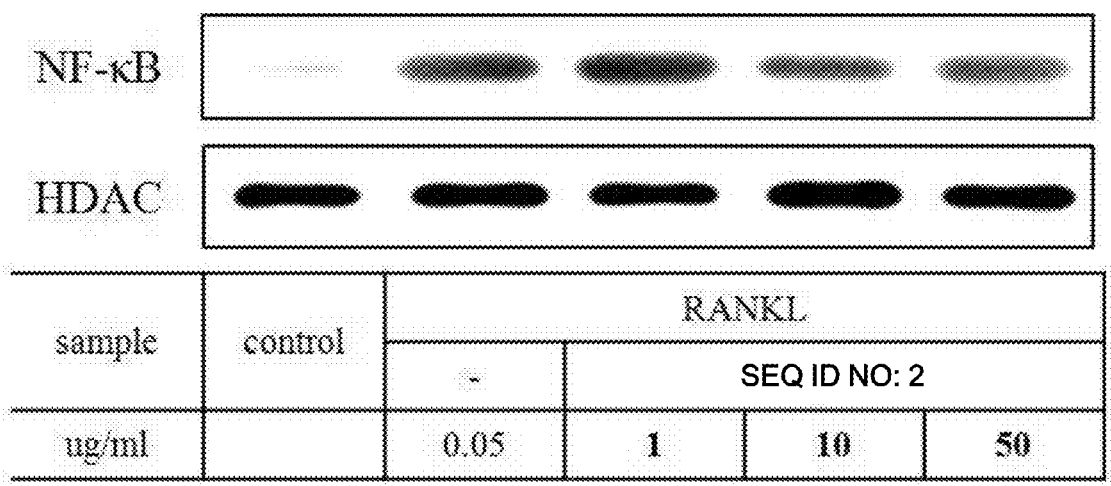
Figure 3C:
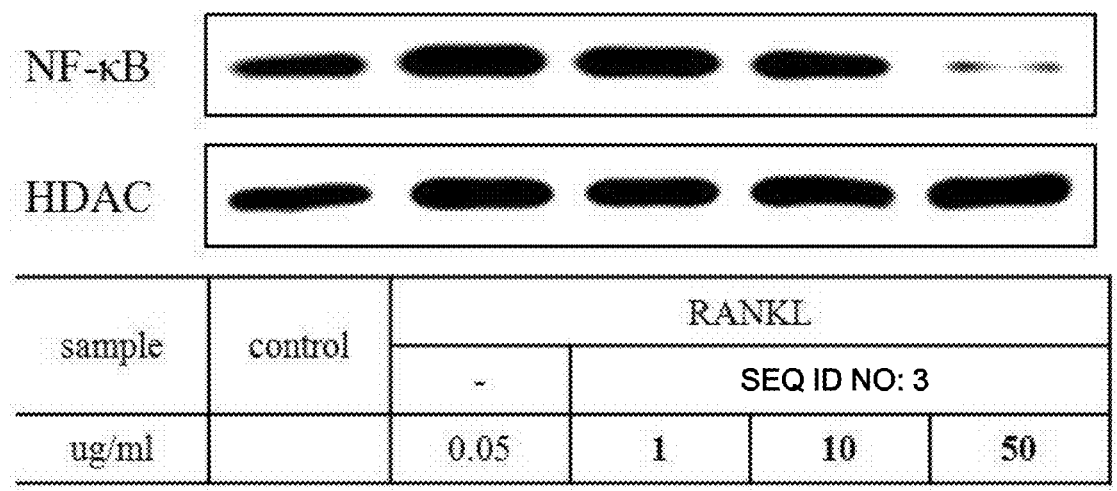

It was observed that the nuclear translocation of NF-κB induced by the treatment with RANKL was reduced by the treatment of the peptides of SEQ ID NO: 1 to SEQ ID NO: 3 (FIGS. 3a to 3c).

Example 4: Immunohistochemistry Staining for TRAP

An attempt was made to more clearly re-verify the expression level of TRAP as a marker expressed during osteoclast differentiation through fluorescent staining and observe the expression reduction tendency thereof by the treatment with the peptides was observed.

Raw 264.7 macrophages were seeded on a 48-well plate at 2×10⁴ cells/well, and at the same time, treated with the materials with different concentrations. Five days after the induction of differentiation, 4% para formaldehyde were added to the cells, and then the cells were incubated and fixed at room temperature for 20 minutes. After the cells were washed three times with PBS, 0.3% Triton X-100 (in PBS) was added, followed by incubation at room temperature for 15 minutes. Thereafter, the cells were washed with PBS three times. Following the addition of 2% BSA (in PBS), the cells were incubated and blocked at room temperature for 1 hour. Primary antibody (TRAP) was diluted in 2% BSA at 1:100, followed by incubation at room temperature for 2 hours. After the cells were washed three times with PBS, the Texas Red, fusion secondary antibody was diluted in 2% BSA at 1:100, followed by incubation at room temperature for 1 hour. Following washing with PBS three times, the cells were mounted using a mounting solution containing DAPI, and the next day, microscopic observation was conducted.

Figure 4A:
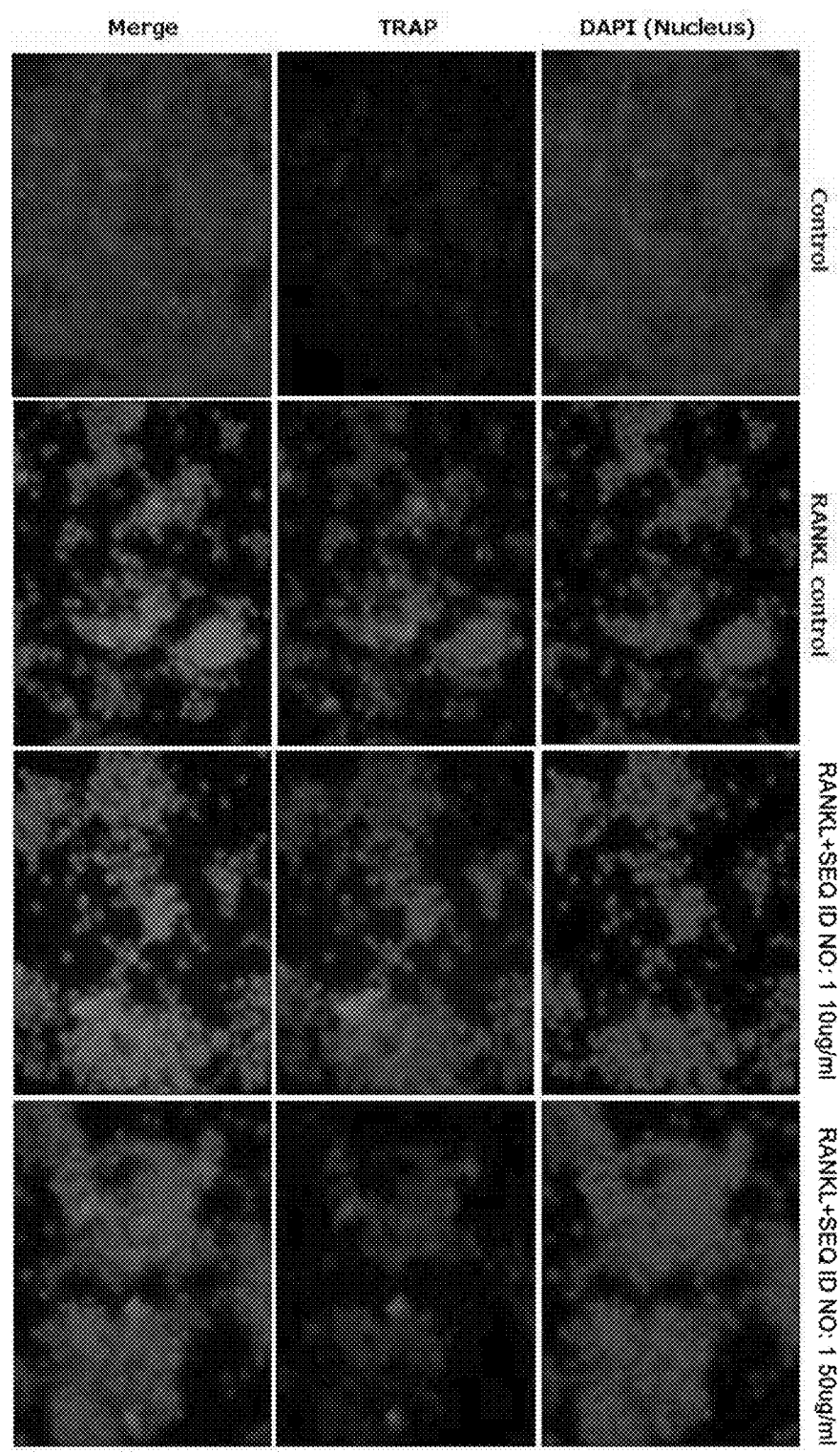
FIG. 4A-4C illustrates immunohistochemistry staining results verifying the expression levels of TRAP expressed during osteoclast differentiation, by the treatment with the peptides of the present invention.
Figure 4B:
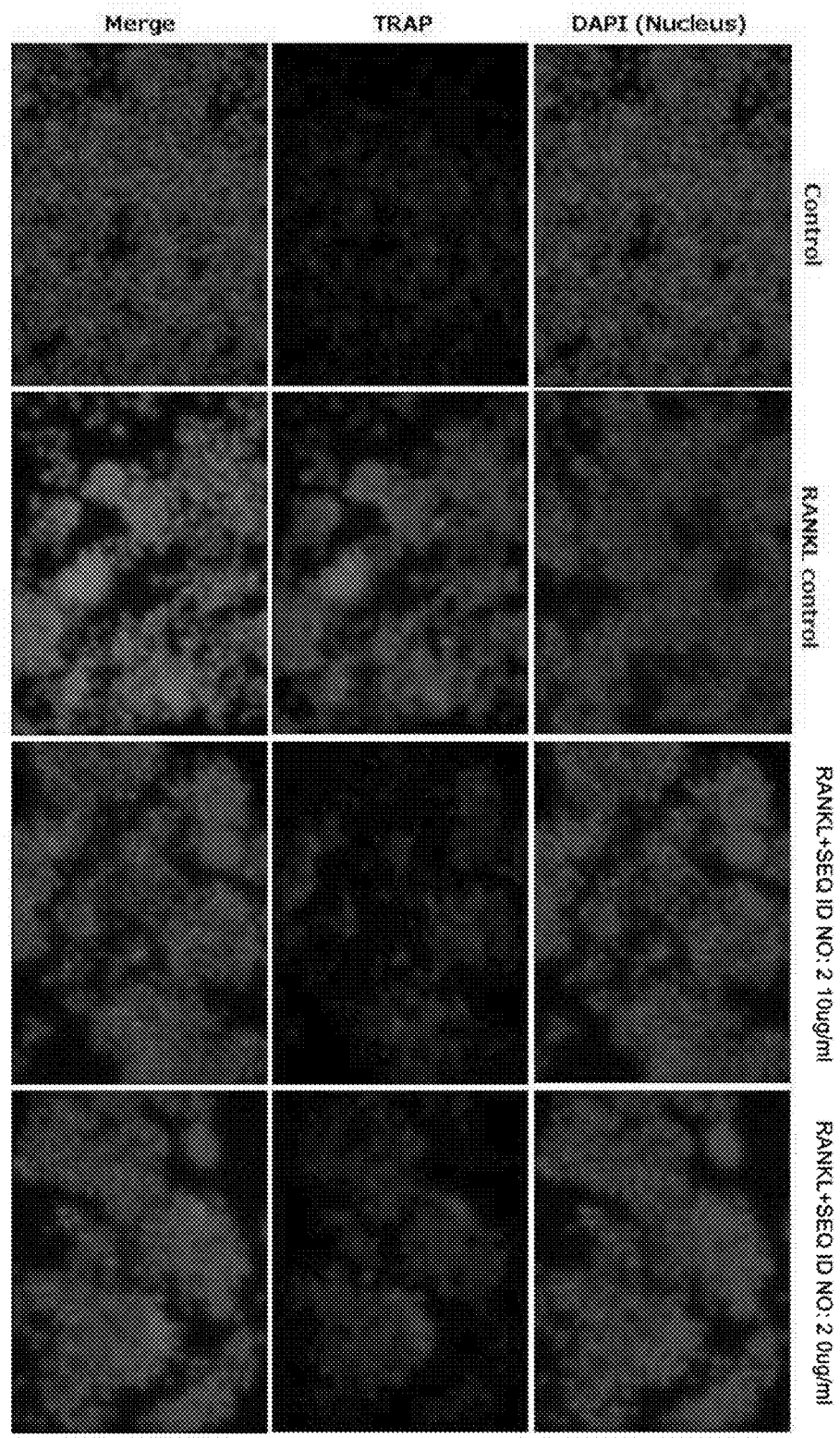
Figure 4C:
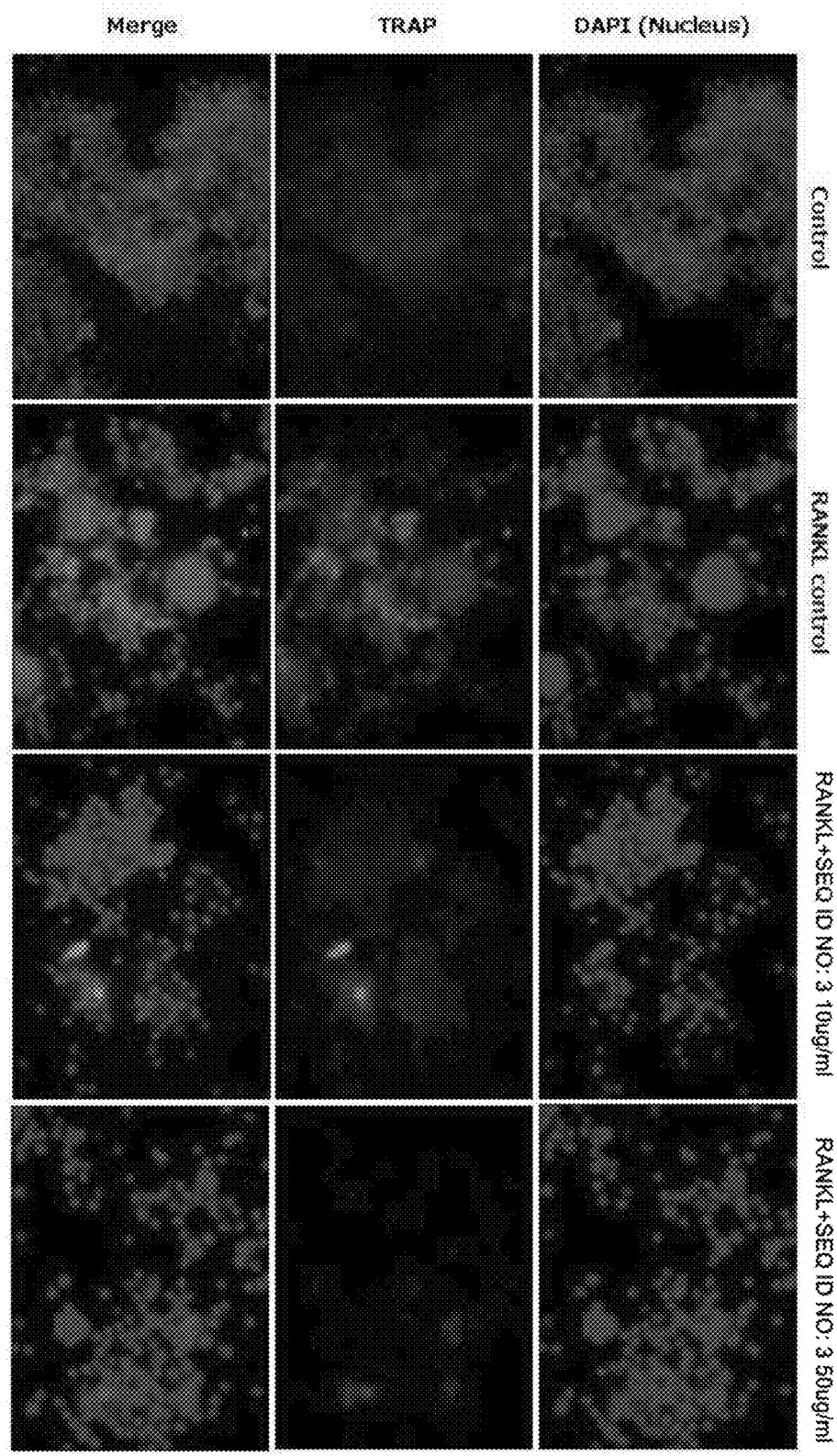

It was observed that, when compared with a control group in which osteoclast differentiation was induced by RANKL treatment to increase TRAP expression, the expression of TRAP was reduced in a concentration-dependent manner for groups treated with peptides of SEQ ID NO: 1 to SEQ ID NO: 3 (FIGS. 4a to 4c).

Example 5: Immunohistochemistry Staining for Cathepsin K

The expression level of Cathepsin K as a marker expressed during osteoclast differentiation was clearly re-confirmed through fluorescent staining, and the expression decrease tendency thereof by the treatment with the peptides was observed.

Raw 264.7 macrophages were seeded in a 48-well plate at 2×10⁴ cells/well, and at the same time, treated with the materials with different concentrations. Five days after the induction of differentiation, 4% para formaldehyde were added to the cells, and then the cells were incubated and fixed at room temperature for 20 minutes. The cells were washed three times with PBS, 0.3% Triton X-100 (in PBS) was added, followed by incubation at room temperature for 15 minutes, and then the cells were washed three times with PBS. Following the addition of 2% BSA (in PBS), the cells were incubated and blocked at room temperature for 1 hour. The primary antibody (Cathepsin K) was diluted in 2% BSA at 1:100, followed by incubation at room temperature for 2 hours. After the cells were washed three times with PBS, FITC-fusion secondary antibody was diluted in 2% BSA at 1:100, followed by incubation at room temperature for 1 hour. Following washing with PBS three times, the cells were mounted using a mounting solution containing DAPI, and the next day, microscopic observation was conducted.

Figure 5A:
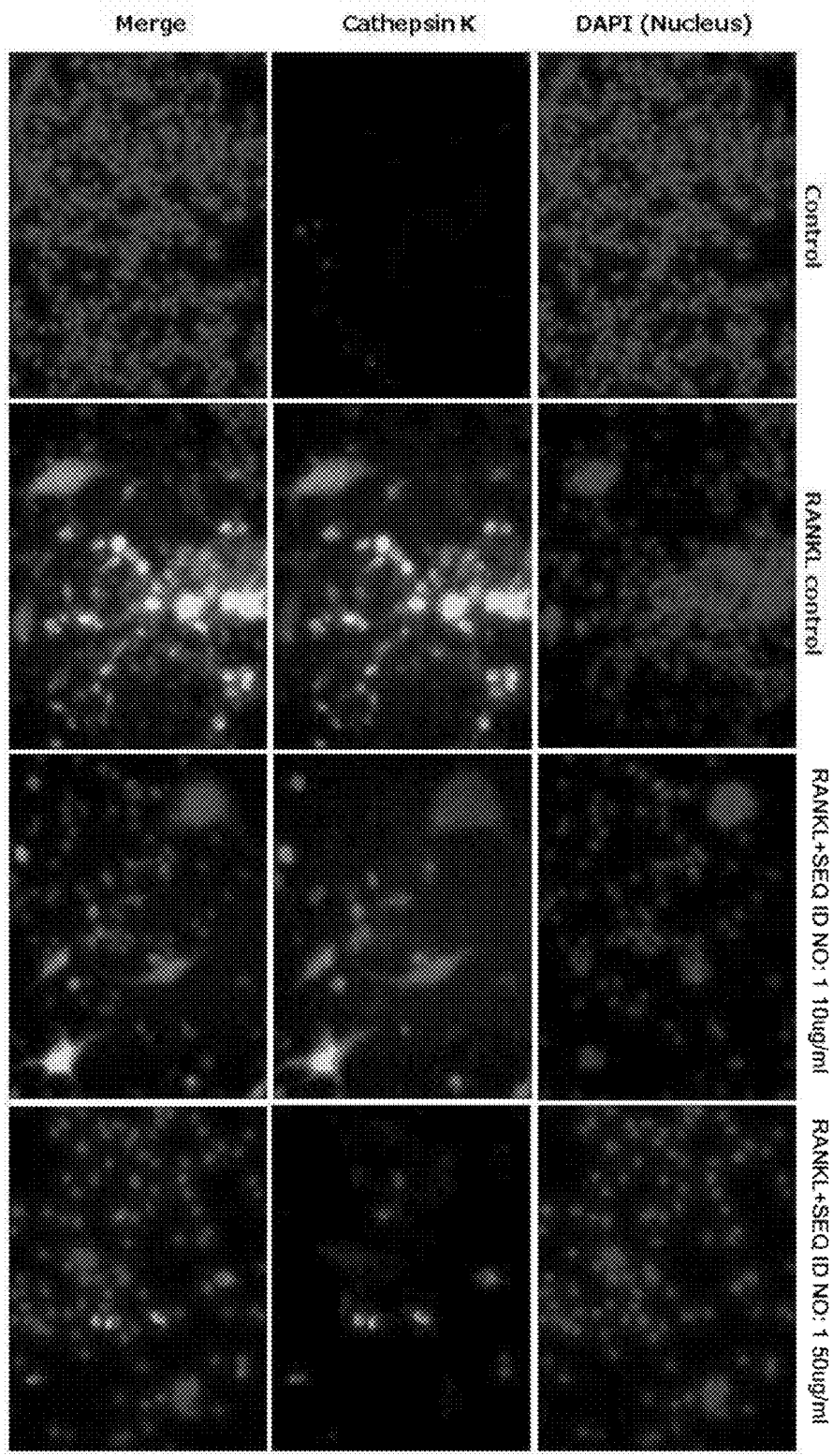
FIG. 5A-5C illustrates immunohistochemistry staining results verifying the expression levels of Cathepsin K expressed during osteoclast differentiation, by the treatment with the peptides of the present invention.
Figure 5B:
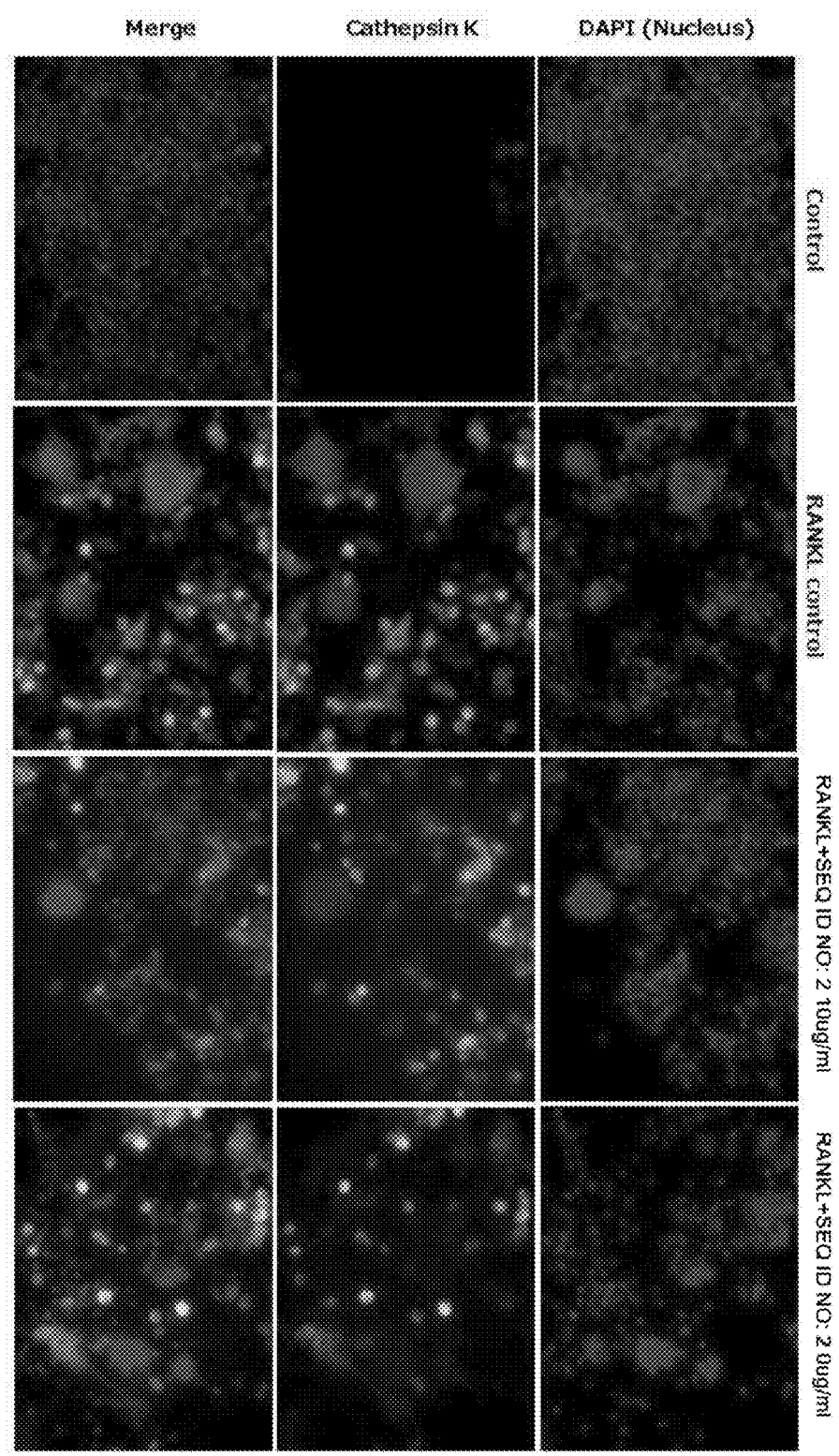
Figure 5C:
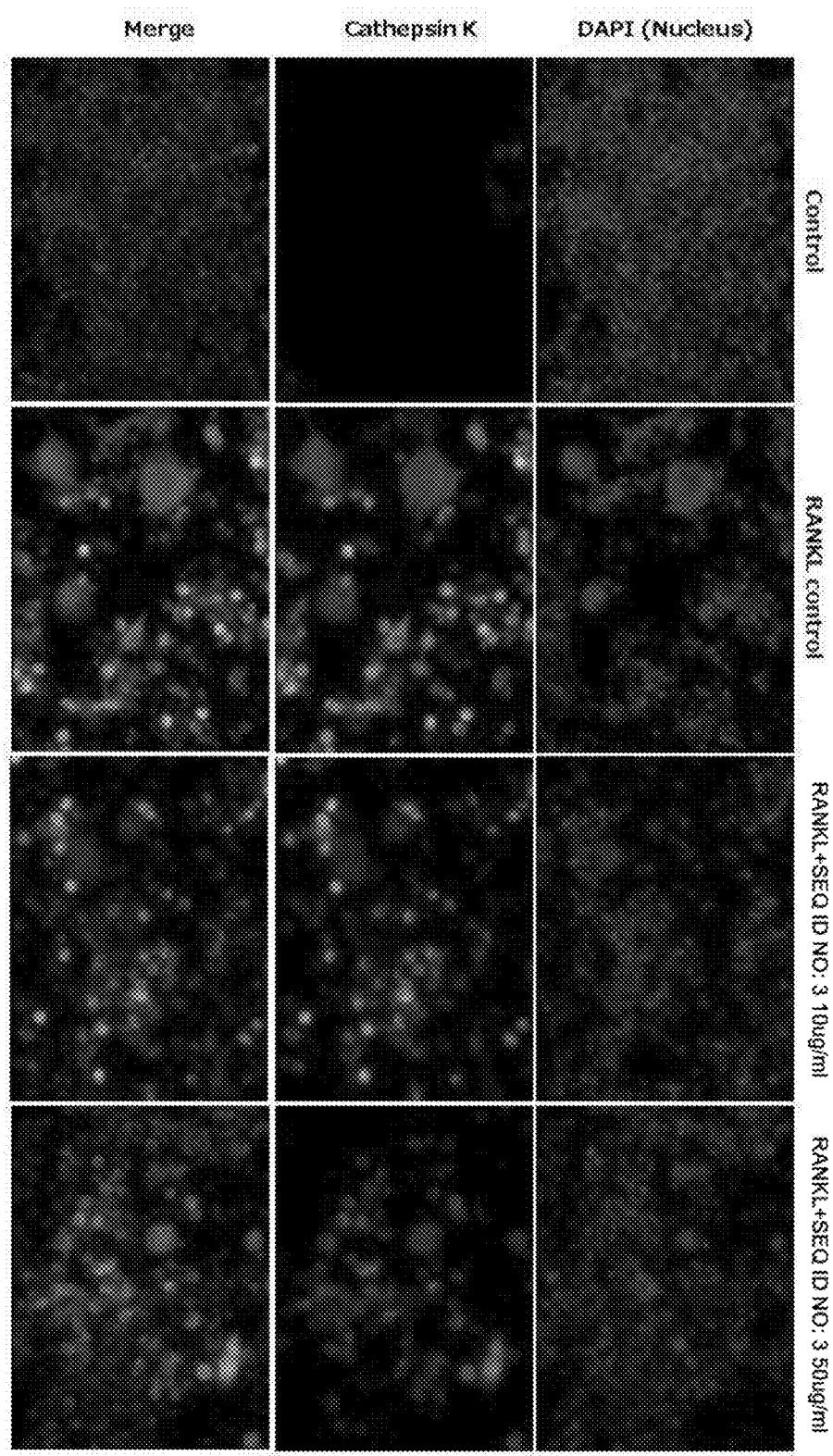

When compared with a control group in which osteoclast differentiation was induced by RANKL treatment to increase Cathepsin K expression, the expression of cathepsin K was reduced in a concentration-dependent manner for groups treated with peptides of SEQ ID NO: 1 to SEQ ID NO: 3 (FIGS. 5a to 5c).

Although the present invention has been described in detail with reference to the specific features, it will be apparent to those skilled in the art that this description is only for a certain embodiment and does not limit the scope of the present invention. Thus, the substantial scope of the present invention will be defined by the appended claims and equivalents thereof.

The invention claimed is:

1. A peptide having an osteoclast differentiation and activity inhibitory ability, the peptide consisting of an amino acid sequence selected from the group consisting of the amino acid sequences of SEQ ID NO: 1 to SEQ ID NO: 3 and, optionally, an N- or C-terminal protecting group.

2. The peptide of claim 1, wherein the peptide reduces the expression of tartrate resistant alkaline phosphatase (TRAP).

3. The peptide of claim 1, wherein the peptide reduces the expression of cathepsin K.

4. The peptide of claim 1, wherein the peptide inhibits the nuclear translocation of NF-κB.

5. A method for preventing or treating a bone disease, the method comprising administering a composition containing a peptide having an osteoclast differentiation and activity inhibitory ability, the peptide consisting of an amino acid sequence selected from the group consisting of the amino acid sequences of SEQ ID NO: 1 to SEQ ID NO: 3 and, optionally an N- or C-terminal protecting group, as an active ingredient to a subject, wherein the bone disease is characterized by insufficient bone formation, mass, or density, or excessive bone resorption.

6. The method of claim 5, wherein the peptide reduces the expression of tartrate resistant alkaline phosphatase (TRAP).

7. The method of claim 5, wherein the peptide reduces the expression of cathepsin K.

8. The method of claim 5, wherein the peptide inhibits the nuclear translocation of NF-κB.

9. The method of claim 5, wherein the bone disease is bone damage, osteoporosis, osteomalacia, rickets, fibrous osteitis, an aplastic bone disease or a metabolic bone disease.

10. The peptide of claim 1, wherein the peptide includes said optional N-terminal protecting group.

11. The peptide of claim 1, wherein the peptide includes said optional C-terminal protecting group.

12. The peptide of claim 1, wherein the peptide lacks said optional N- and C-terminal protecting groups.

13. The peptide of claim 1, wherein said optional N- or C-terminal protecting group is selected from the group consisting of an acetyl group, a fluorenyl methoxy carbonyl group, a formyl group, a palmitoyl group, a myristyl group, a stearyl group, and polyethylene glycol (PEG).

14. The method of claim 5, wherein the peptide includes said optional N-terminal protecting group.

15. The method of claim 5, wherein the peptide includes said optional C-terminal protecting group.

16. The method of claim 5, wherein the peptide lacks said optional N- and C-terminal protecting groups.

17. The method of claim 5, wherein said optional N- or C-terminal protecting group is selected from the group consisting of an acetyl group, a fluorenyl methoxy carbonyl group, a formyl group, a palmitoyl group, a myristyl group, a stearyl group, and polyethylene glycol (PEG).

* * * * *

SEQUENCE LISTING

```
<160> NUMBER OF SEQ ID NOS: 3

<210> SEQ ID NO 1
<211> LENGTH: 7
<212> TYPE: PRT
<213> ORGANISM: Artificial Sequence
<220> FEATURE:
<223> OTHER INFORMATION: Peptide 1

<400> SEQUENCE: 1

Ser Pro Val Glu Phe Leu Arg
1               5

<210> SEQ ID NO 2
<211> LENGTH: 9
<212> TYPE: PRT
<213> ORGANISM: Artificial Sequence
<220> FEATURE:
<223> OTHER INFORMATION: Peptide 2

<400> SEQUENCE: 2

Ile Thr Leu Gln Glu Ile Ile Arg Thr
1               5

<210> SEQ ID NO 3
<211> LENGTH: 10
<212> TYPE: PRT
<213> ORGANISM: Artificial Sequence
<220> FEATURE:
```

```
<223> OTHER INFORMATION: Peptide 3

<400> SEQUENCE: 3

Ala Cys Ile His Thr Leu Ser Leu Leu Cys
1               5                   10
```